Figure 1:
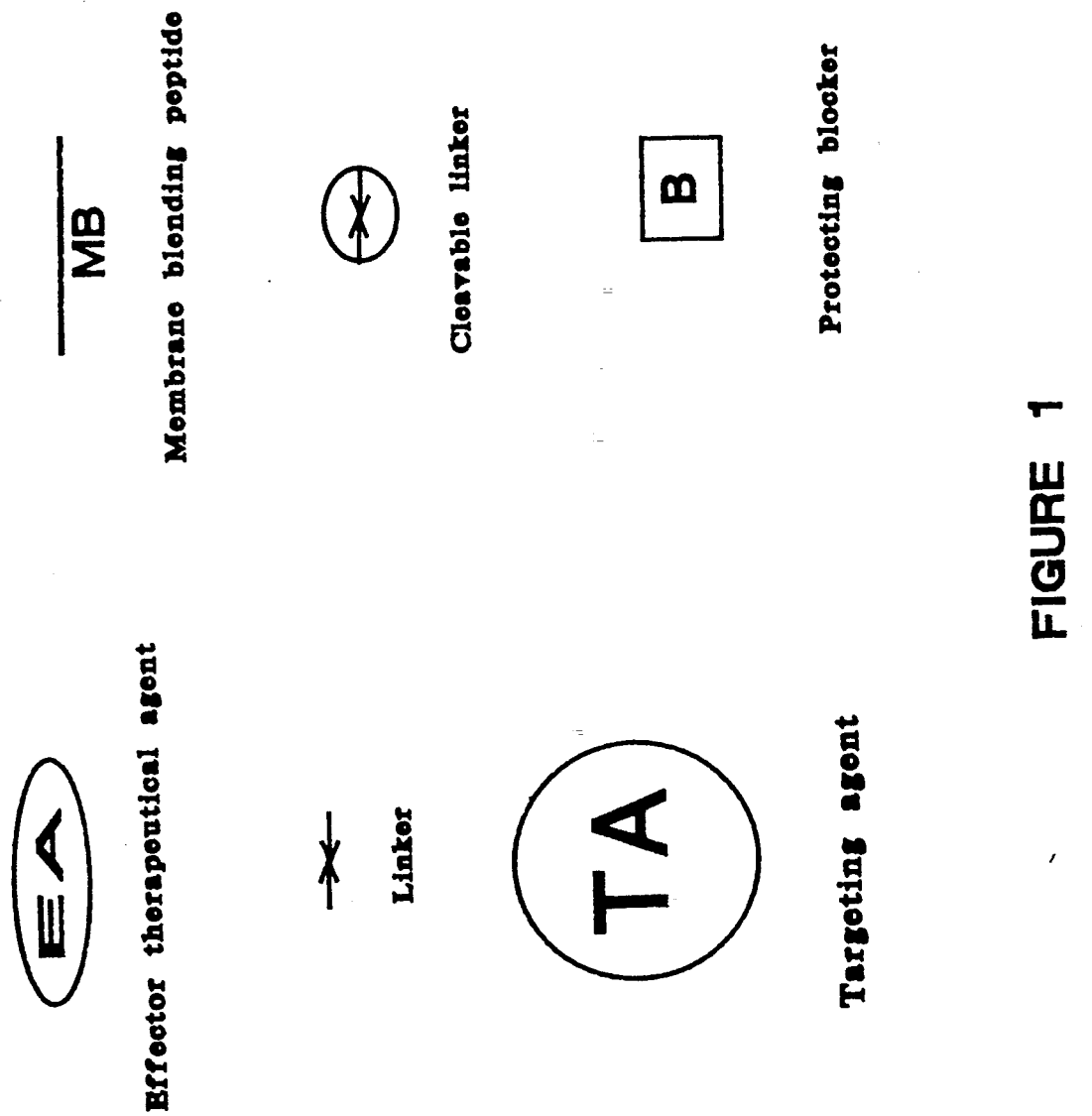

United States Patent [19]

Chang et al.

[11] Patent Number: 5,149,782
[45] Date of Patent: Sep. 22, 1992

[54] MOLECULAR CONJUGATES CONTAINING CELL MEMBRANE-BLENDING AGENTS

[75] Inventors: Tse-wen Chang; Jean deVilliers; Wayne Gordon, all of Houston, Tex.

[73] Assignee: Tanox Biosystems, Inc., Houston, Tex.

[21] Appl. No.: 234,399

[22] Filed: Aug. 19, 1988

[51] Int. Cl.$^5$ .......................... C07K 7/10; C07K 17/02
[52] U.S. Cl. ................................... 530/326; 530/322; 530/324; 530/345; 530/377; 530/391.1; 530/391.7; 530/391.9; 530/408; 530/409; 530/410; 536/27; 536/28; 536/29
[58] Field of Search ............... 530/390, 391, 408, 409, 530/326, 324, 322, 345, 377, 410, 391.1, 391.7, 391.9; 536/27, 28, 29

[56] References Cited

U.S. PATENT DOCUMENTS

| | | | |
|---|---|---|---|
| 4,362,716 | 12/1982 | Bouchandon et al. | 514/19 |
| 4,664,911 | 5/1987 | Uhr et al. | 424/85.91 |
| 4,731,324 | 3/1988 | Huang et al. | 435/5 |
| 4,859,769 | 8/1989 | Karlsson et al. | 536/53 |
| 4,892,827 | 1/1990 | Pastan et al. | 435/19 |
| 4,894,443 | 1/1990 | Greenfield et al. | 530/388 |

FOREIGN PATENT DOCUMENTS 0317957  5/1989  European Pat. Off. .

OTHER PUBLICATIONS

Byers et al., Abstract No. 942.
Splitler et al., (1987) Cancer Research 47:1717–1723.
Pierce Catalog p. A-10 "Trault's Regent".
Hwang et al., (1987) Cell 48:129–136.
Marsh J. W. et al., "A Flexible Peptide Spacer Increases the efficacy of Holoricin Anti-T cell Immunotoxins" J. Immunol. 140:3674–3678 (1988).
Griffin, T. W. et al., "Antitumor Activity of Intraperitoneal Immunotoxins in a Nude Mouse Model of Human Malignant Mesothelioma" Cancer Research 49: 4266–4270 (1987).
Neville, D. M. Jr., et al., "Enhancement of Immunotoxin Efficacy by Acid-Cleavable Cross-Linking. Agents Utilizing Diptheria Toxin and Toxin Mutants" J. Biological Chemistry 264:14653–14661 (1989).
Olsnes S., et al., "Immunotoxins–entry into cells and Mechanisms of action" Immunology Today 10:291–295 (1989).
Chovnick, A., et al., "A Recombinant, Membrane-acting Immunotoxin" Cancer Research 51:465–467 (1991).
May, R. D., et al., "Evaluation of Ricin A Chain-Containing Immunotoxins Directed Against Different Epitopes on the S-chain of Cell Surface-Associated IgD on Murine B Cells" J. Immunology 144:3637–3642 (1990).
Kabanov, A. V., et al., "Fatty Acylation of Proteins for Translocation Across Cell Membranes" Biomedical Science 1:33–36 (1990).
Schmidt, MFG, "Fatty Acylation of Proteins" Biochimica et Biophysica Acta 988:411–426 (1989).

(List continued on next page.)

Primary Examiner—Christine M. Nucker
Assistant Examiner—Kay Kim
Attorney, Agent, or Firm—Eric P. Mirabel; Giulio A. DeConti, Jr.

[57] ABSTRACT

Molecular conjugates which facilitate the attachment of macromolecular drugs onto cellular surfaces and their entry into cells are described. The molecular conjugates comprise a macromolecular drug linked to an "inactivated" membrane blending agent which inserts into the cellular plasma membrane. The membrane blending agent is inactivated by cleavable linkage to a blocking agent which, until released from the conjugate under appropriate conditions, blocks and ability of the membrane blending agent to insert into the cellular membrane. Upon release of the blocking agent, the membrane blending agent is "activated" and the conjugate can be inserted into a cellular plasma membrane. The membrane blending agents can be peptides such as fusogenic or ion channel forming peptides or long chain fatty acids. The blocking agents can be bulky or charged moieties which mask and prevent insertion of the membrane blending agent.

11 Claims, 4 Drawing Sheets

Conjugate I

Conjugate II

Conjugate III

Conjugate IV

OTHER PUBLICATIONS

Hu, J. S., et al., "Protein Fatty Acylation: A Novel Mechanism for Association of Proteins with Membranes and its Role in Transmembrane Regulatory" *Biofactors* 1:219-226 (1988).

Vander Wiele, F. C., et al., "Site-Specific E-NH$_2$ Monoacylation of Pancreatic Phospholipase A$_2$, 2, Transformation of Soluble Phospholipase A$_z$ into a Highly Penetrating Membrane-Bound Form" *Biochemistry* 27:1688-1694 (1988).

Huang, A., et al., "Monoclonal Antibody Covalently Coupled with Fatty Acid" *J. Biological Chemistry* 255:8015-8015 (1980).

Thorpe P. E., et al., "Improved Antitumor Effects of Immunotoxins Prepared with Deglycosylated Ricin A-Chain and Hindered Disulfide Linkages" *Cancer Research* 48:6396-6403 (1988).

Diaz, R. E. C., et al., "Activation of Bee Venom Phospholipase A$_2$ 124 Oleoyl Imidazolide produces a thiol- and proteinaseresistant conformation" *Biochimica et Biophysica Acta* 830:52-58 (1985).

Sandvig, K, et al., "Diphtheria Toxin-induced Channels in Vero Cells Selective for Monovalent Cations". *J. Biological Chemistry* 263:12352-12359 (1988).

Mozhaev, V. V., et al., "Protein Stabilization via hydrophilization" *Eur. J. Biochem* 173:147-154 (1988).

Faro-Rivas, J., et al., "Capping and Co-Capping of Membrane Immunoglobulin and Lipid-Conjugated Immunoglobulin Inserted in the Cell Membrane of B Lympocytes" *Scand. J. Immunol.* 30:435-440 (1989).

Peacock, J. S. et al., "Biological Acting of Antigen Receptors Artifically Incorporated onto B Lymphocytes" J. Immunol. 137:1916-23 (1986).

Grant, S. R., et al., "A Model System for Studies of Specific membrane Interactions" *Biochemistry* 21:1274-1279 (1982).

Vanderwiele, F. C., et al., "Site-Specific E-NH$_2$ Monoacylation of Pancreatic Phospholipase A$_2$I. Preparation and Properties" *Biochemistry* 27:1683-1688 (1988).

Brochure by Immunogen, Inc.

Thorpe, P. E. et al. "Blockade of Galactose-Binding Sites of Ricin by its Linkage to Antibody" Eur. J. Biochem. 140 63:71 (1984).

George S. K. et al., "Development of a Universal Membrane Targeting System" Protein Engineering and Production, Bio/technology (1988).

Pellman, D. "An N-Terminal Peptide from p60 spc ..." Nature 314:374-77 (1985).

George et al., Proc. 1988 Miami Bio/Technology Winter Symposium, IRL press, Washington, D. C., p. 33 Feb. 8-12, 1988.

Pasten et al., *Cell*, 47:641-648 (1986).

Gallaher et al., *Cell*, 50:327-328 (1987).

White et al., *Quarterly Rev. Biophysics*, 16:151-195 (1983).

Gething et al., *J. Cell Bio.*, 102:11-23 (1986).

Guy, *Biophysics J.*, 45:249 (1984).

Finer-Moore and Stroud, Proc. Natl. Acad. Sci., USA, 81:155 (1984).

Greenblatt et al., FEBS Letter, 193:125 (1985).

Lear et al., *Science*, 240:1177-1181 (1988).

Schlessinger, *Ann. Rev. Biochem.*, 50:193-206 (1981).

Magee et al., *Biochem. Biphys. Acta*, 798:156-166 (1984).

Streuli and Griffin, *Nature*, 326:619-622 (1987).

Chow et al., *Nature*, 327:482-486 (1987).

Pellman et al., *Nature*, 314:374-377 (1985).

Vitetta et al., *Science*, 238:1098-1104 (1987).

MOLECULAR CONJUGATES CONTAINING CELL MEMBRANE-BLENDING AGENTS

BACKGROUND

Many proteins, such as certain plant and microbial toxins are potentially very powerful therapeutical agents for treating cancer and other diseases. Nucleic acids (DNA and RNA) are also potentially very versatile agents for treating viral diseases and genetic diseases. Because these macromolecules act on intracellular components to achieve their cytocidal, cytostatic, or specific regulatory effects, therapeutic efficacy depends on the ability of these molecules to get into cells.

Some macromolecules, including proteins, DNA, and RNA are known to be able to enter cells. In defined in vitro experiments, in which a protein, such as pokeweed antiviral peptide, ricin A chain, and other plant toxins are incubated with cells, a small fraction of the protein somehow passes through the cellular plasma membrane and inhibits certain synthetic pathways, leading to cell malfunction and death. Nucleic acid molecules can also enter calls under certain not-well-defined conditions. In routine transfection procedure, cells are incubated with DNA of specific genes and acquire specific genetic changes. Oncogenic DNA can enter cells, be inserted into host genome and transform cells. Anti-sense RNA enters cells and inhibits the expression of specific genes. Double-stranded DNA or mismatched double-stranded RNA can also get into cells to induce certain antiviral effects including interferon production.

It is not entirely clear how various types of macromolecules enter cells. In the case of some plants toxins, binding to the cell surface and translocation mechanisms across the membrane are involved. For example, when intact ricin, which is composed of two chains, the A and B chains, react with cells, the B chain binds to certain carbohydrate moieties on the surface of the cellular membrane and, by some unknown mechanism, facilitates the entry of the A chain into a cell. The A chain inactivates ribosomes, interferes protein synthetic pathways and cause the death of the cells. The A chain alone can penetrate cells but it does so very poorly and much higher concentrations (as compared to intact ricin molecules) are required. In the case of nucleic acid molecules, precipitation by calcium phosphate or by polyethylene glycol can enhance their entry into cells.

Although the exact mechanisms by which proteins, DNA and RNA enter cells are not well understood, it is likely that association with cellular membrane enhances entry into the cell. Further, pinocytosis has been proposed to play an important role, and it is known that the association of molecules with the cell membrane will enhance the endocytosis of the molecules by the cells.

Recently, George et al. (Proc. 1988 Miami Bio/Technology Winter Symposium, p. 33, IRL Press, Washington, D.C.) proposed a means for introducing diagnostically and therapeutically useful agents onto cellular surfaces. Exploiting the inherent ability of the carboxy terminal portion of cytochrome $b_5$ to insert into cellular membranes, the authors suggest the coupling of this peptidic segment to other proteins to enable them to acquire this property.

SUMMARY OF THE INVENTION

This invention pertains to improved compositions and methods for enhancing the association of macromolecular drugs with cell membranes and for enhancing the association and entry of macromolecular drugs into cells in order to improve drug efficacy. In particular, the invention pertains to molecular conjugates which comprise a macromolecular drug (such as a protein or a nucleic acid) coupled to a membrane blending agent which can insert into the lipid bilayer of cellular membranes. The membrane blending agent is coupled to a blocking agent which, until released, blocks the ability of the membrane-blending agent to insert into the membrane. The linkage between the membrane blending agent and the blocking agent is cleavable under appropriate conditions. Upon release of the blocking agent, the membrane blending agent is activated and molecular conjugate is inserted into the cellular membrane. Membrane blending agents can be peptides such as appropriate regions of certain proteins which insert into cellular membranes. Examples include fusogenic polypeptides, ion-channel forming polypeptides and other membrane polypeptides. Membrane blending agents can also be long chain fatty acids. Examples are myristic acid (tetradecanoic acid), palmitic acid (hexadecanoic acid), or other fatty acids of varied lengths. The blocking agent when linked to the membrane blending agent, inhibits the membrane blending agent to insert into the plasma membrane of cells. It is a hydrophilic group or an electrically charged group. The blocking agent can also serve a second purpose; it can be a targeting agent (such as an antibody or a ligand for a cell surface receptor) which can serve to target the molecular conjugate to a desired cell or cell population. Examples are monoclonal antibodies specific for tumor-associated cell surface antigens expressed on tumor cells or for virus-specific antigens expressed on the surface of virus-infected cells. Other examples are interleukin-2 which binds interleukin-2 receptors, and recombinant soluble CD4 antigen which binds to envelope glycoprotein gp120 of HIV-1 expressed on the surface of virions and HIV-1-infected cells. If no other purpose is to be conferred by the blocking agent, the blocking agent is preferably small, for example amino acids or short peptides. The short peptides may be Cys-Glu, or Cys-Glu-Glu.

This invention also pertains to the therapeutic use of membrane blending agents themselves. For this purpose, membrane blending agents can be cleavably linked to blocking agents which block the activity of the agent until released at the intended site of activity. In addition, two or more membrane blending agents can be interlinked as therapeutic conjugates.

BRIEF DESCRIPTION OF THE DRAWINGS

FIG. 1 shows the schematic symbols of the components used in constructing conjugates that employ membrane blending agents.

FIG. 2 shows the representative structure of the conjugates with active or inactive (precursor) forms of membrane blending agents.

FIG. 3 shows representative molecular conjugates containing membrane blender agents as potential therapeutical agents.

FIG. 4 shows the various types of crosslinkers composing membrane blending agents and functional linking groups.

DETAILED DESCRIPTION OF THE INVENTION

Molecular conjugates of this invention comprise;

a. a macromolecular drug coupled to:

b. a membrane blending agent which can insert itself into a cellular membrane, which, in turn, is coupled to;
c. a blocking agent which prevents the membrane blending agent from inserting into the cellular membrane.

In the conjugates, the membrane blending agent is usually irreversibly linked to the drug. The blocking agent is cleavably linked to the membrane blending agent such that it is released under appropriate conditions, and upon such release the membrane blending agent is activated for insertion into the cellular membrane. The components of the molecular conjugates, and their interrelated function are discussed in detail below. Although the molecular conjugates are designed primarily for enhanced entry into cells, penetration into the cell may not always be necessary, depending upon the design of the conjugates and intended biological effect. The attachment of the molecular conjugates to the cellular membrane can bring about certain biological and therapeutical effects even though the molecules do not actually enter the cells.

1. Macromolecular drugs

The macromolecular drug components of the molecular conjugates of this invention can be proteins, glycoproteins, nucleic acids and other large organic molecules, such as tricathecums. As examples, potential therapeutical agents include plant toxins, such as ricin (A chain), abrin (A chain) pokeweek antiviral peptide, saporin, and gelonin, microbial toxins, pseudomonas exotoxin A, and diptheria toxin (reviewed by Pastan, I. et al. (1986) *Cell* 47:641-648). Many of these substances have been employed in constructing immunoconjugates, see for example, Viosin, G. et al., U.S. Pat. No. 4,340,535, 1982; Masuho, Y. et al., U.S. Pat. No. 4,379,145, 1983, Jansen, F. K. et al., U.S. Pat. No. 4,414,148, 1983; Pastan, I., et al., U.S. Pat. No. 4,545,985, 1985; Casellas, P. et al., U.S. Pat. No. 4,643,895, 1987; Uhr, J.W. and Vitetta, E. S., U.S. Pat. No. 4,664,911, 1987; Collier, R. J. and Carroll, S. F., U.S. Pat. No., 4,709,017, 1987.

The nucleic acids include double stranded DNA or mismatched double stranded RNA. These substances have been used as interferon inducers, anti-viral agents, or anti-tumor agents. Therapeutical nucleic acids also include DNA segments of specific genes for gene transfer or gene therapy. Anti-sense RNA can also be used to inhibit specific gene expression.

2. Agents with affinity for cell surface or membrane

The membrane blending agents, can be peptides, fatty acids., or other molecules which have an ability to insert into cellular plasma membranes. Preferred agents are peptides, peptidic segments and fatty acids.

Several kinds of peptidic segments in protein molecules or synthetic peptides are known to be associated with the cellular plasma membrane. In general, these peptides contain hydrophobic amino acid residues. The peptides can insert or embed into the lipid bilayer of cellular plasma membranes. These peptides or peptidic segments can be derived from the following types of peptides:

A) Fusogenic peptides: Certain enveloped viruses infect target cells and cause the fusion among infected cells or among infected and uninfected cells, forming giant multi-nucleated cells, called syncytia. Various experiments have indicated that the fusion is mediated by a protein expressed on the surface of virion particles and infected cells. Gallaher, W. R. et al. (1987) *Cell* 50:327-328; White, J., et al. (1983) *Quarterly Rev. Biophysics* 16:151-195, 1983; Gething, M. et al. (1986) *J. Cell Biology* 102:11-23. Mutations of the fusion proteins can abolish the infectivity of the viruses and their ability to form syncytia. Transfection of genes encoding the fusion protein into cells can cause these cells to fuse. Mutational analyses and transfectional studies have identified the peptidic segments responsible for fusion. Synthetic peptides, representing the fusogenic peptidic segments, can block the fusion. Amino acid sequence analyses among the fusion proteins of various syncytia forming viruses have revealed that the peptidic segments range from 10 to 30 amino acid residues in length and are hydrophobic. They are located either at the amino terminus or internally, within the polypeptides of the fusion protein. The fusion proteins of several viruses contain repetitious Phe-X-Gly sequences, in which X is a nonpolar amino acid residue.

B) Amphiphilic ion channel-forming peptides: The transmembrane peptidic segments of ion channel-forming proteins have unique L-helical structures. All channels are formed by four or five of such homologous domains. These peptidic segments contain polar and nonpolar residues. The polar residues line up on one face of the helices. These polar sides of the composed helices form the channels for ion transfer. The remaining sides of the helices interact among one another and with the lipid bilayer. Guy, H. R. (1984) *Biophysics J.* 45:249; Finer-Moore, J. and Stroud, R. (1984) *Proc. Natl. Acad. Sci. . U.S.A.* 1:155; and Greenblatt, R. E. et al. (1985) *FEBS letter* 193:125. Recently, peptides of 21 amino acids long, which have the structure of $H_2N$-(Leu-Ser-Leu-Leu-Leu-Ser-Leu)$_3$-$CONH_2$ have been synthesized and shown to form functional ion channels. Lear, J. D. et al. (1988) *Science* 240:1177-1181.

It is important to point out that in cases where the membrane blending agents themselves are not used as the therapeutical agents, it is not the ion channel-forming or membrane fusion properties that are of interest, it is the property to insert or to embed into the lipid bilayer of cell membrane that is of interest. In fact, it is preferred that the effector or therapeutical agents do not associate with the membrane too strongly, so that they can be liberated into the cells during the translocation process. Thus, it is therefore adequate that only segments of the ion channel-forming peptides are used. For example, a peptidic segment of ten amino acid residues:

$HN_2$-Leu-Ser-Leu-Leu-Leu-Ser-Leu-Leu-Ser-Leu-$CONH_2$.

C) Other peptides with affinity for membrane lipids: Peptidic segments of some other peptides are known to enable proteins to become embedded within the lipid bilayer of cellular membrane. An example is the hydrophobic C-terminal peptidic segment of cytochrome $b_5$ (mentioned above). See George, S. et al. in *Proc.* 1988 *Miami Bio/Technology Winter Symposium,* p.33, IRL Press, Washington, D.C.. These peptides blend into the membrane because of the properties of the peptides. The process does not involve catalysis mediated by enzymes. The transmembrane regions of most integral membrane proteins contain hydrophobic and non-charged residues. These peptidic segments can also be used. For example, a segment of the transmembrane region of membrane-bound IgE. An adequate segment is a segment 11 amino acid residues long:

H$_2$N-Leu-Trp-Thr-Ser-ILe-Cys-Val-Phe-Ile-Thr-Leu-CONH$_2$.

D) Some long chain fatty acids, such as palmitic acid (hexadecanoic acid; Schlessinger, M. (1981) *Ann. Rev. Biochem.* 50:193–206; Magee, A. et al. (1984) *Biochemica Biophysica Acta* 798:156–166) and myristic acid (tetradecanoic acid; Streuli, C. H. and Griffin, B. E. (1987) *Nature* 326:619–622; Chow, M. et al. (1987) *Nature* 327:482–486) are found to conjugate to protein molecules. It has been suggested that the modification of proteins with fatty addition may facilitate the association of proteins with cellular membrane (Pellman, D. et al. (1985) *Nature* 314:374–377). Thus, the fatty acid can serve a membrane blending agent in the molecular conjugates of this invention. Chemical modification can be made to introduce linking groups to the long chain fatty acids as described below.

3. Linking membrane blender peptides in inactive or "precursor" forms to macromolecules Membrane blending agents can be linked to a macromolecular drug through functional groups endogenous to the membrane blending agent or through functional groups introduced into the membrane blending agent or into the drug. Usually, the membrane blending agent is irreversibly linked to the drug (in certain circumstances the linkage may be cleavable). For example, membrane-blending peptides can be linked to protein molecules by employing the many functional groups on the protein molecules, such as NH$_2$ or SH. Nucleic acids can be modified to contain active groups through which a membrane-blending agent can then be linked. Alternatively, genetic engineering methods can also be used to link a membrane blending peptide to proteinaceous macromolecular drug. The peptide can be genetically fused to the drug. Oligonucleotide encoding a membrane blending peptide can be linked (either at a terminus or internally) to the gene encoding the therapeutical protein. The composite gene can then be expressed in an appropriate host system to produce the protein conjugates containing the membrane blending peptides.

Because most therapeutical macromolecular drugs, such as cytotoxins for tumors, are designed to target certain tissues, it is desirable that the drug acquire the ability to associate with cellular membrane only when it reaches to the target tissue or cells. If a drug is conjugated to a membrane blending peptide that is in active form, this conjugate, after administration into the recipient, may associate with cells nonselectively. For example, the conjugates could associate with cells in the blood or in the vasculature. Further, the exposed membrane blending peptides may be susceptible to proteolytic cleavage in the circulation. These complications will decrease the therapeutical efficacy and increase toxic effects of the drugs.

To reduce these complications, macromolecular drugs are coupled to membrane blending peptides in forms in which the membrane blending agent is not active. The preparation of inactive or "precursor" form of the molecular conjugates can be achieved by "masking" the membrane blending agent such that it is blocked from inserting into the cellular plasma membrane. This can be achieved by linking one end of the membrane blending agent to the drug and by cleavably linking another part of the membrane blending agent to a masking or blocking agent. The blocking agent can be a bulky or an electrically charged moiety. It may be an amino acid, peptide or protein. It is preferable that the blocker does not induce immune responses in humans. The attachment of the bulky or charged moiety to the membrane blending agent is designed to prevent its insertion into the cellular membrane and thus, prevent association of the conjugate with the cellular membrane.

The blocking agent can also be designed to serve a second purpose. The blocking agent can also be a targeting agent which selectively directs the molecular conjugate to an appropriate target. For example, the targeting agent may be an antibody specific for a unique antigenic epitope of a diseased cell such as a tumor cell, or a virus-infected cell. Pastan, I. et al. (1986) *Cell* 47:641–648; Vitetta, E. S. et al. (1987) *Science* 238:1098–1104. The targeting agent may also be a ligand for a cell surface receptor (for example, a hormone or growth factor) or soluble forms receptors for viral antigens.

The membrane blending agents are linked to the blocking agent by a cleavable linkage. The blocking agent is released under appropriate conditions (e.g., conditions extant at the target site) and the release activates the membrane blending agent.

A preferred cleavable linkage is a disulfide bond. The disulfide bond may be found between the SH group of Cys residues in a protein molecule and active electrophilic S atoms introduced into the membrane blending agents. For example, the electrophilic S atom can be introduced by N-succinimidyl 3-(2-pyridyldithio) propionate (SPDP). At the target tissues sites, the S—S bonds are cleaved, when they are gradually reduced. Cleavable bonds can also be constructed taking advantage of the slight acidic pH in target tissues. Bonds sensitive to light radiations can also be constructed. In therapeutical uses, the molecular conjugates containing the inactive precursor forms of membrane blending agents are administered in conjunction with certain radiations which cleave the bonds.

Figure 2:
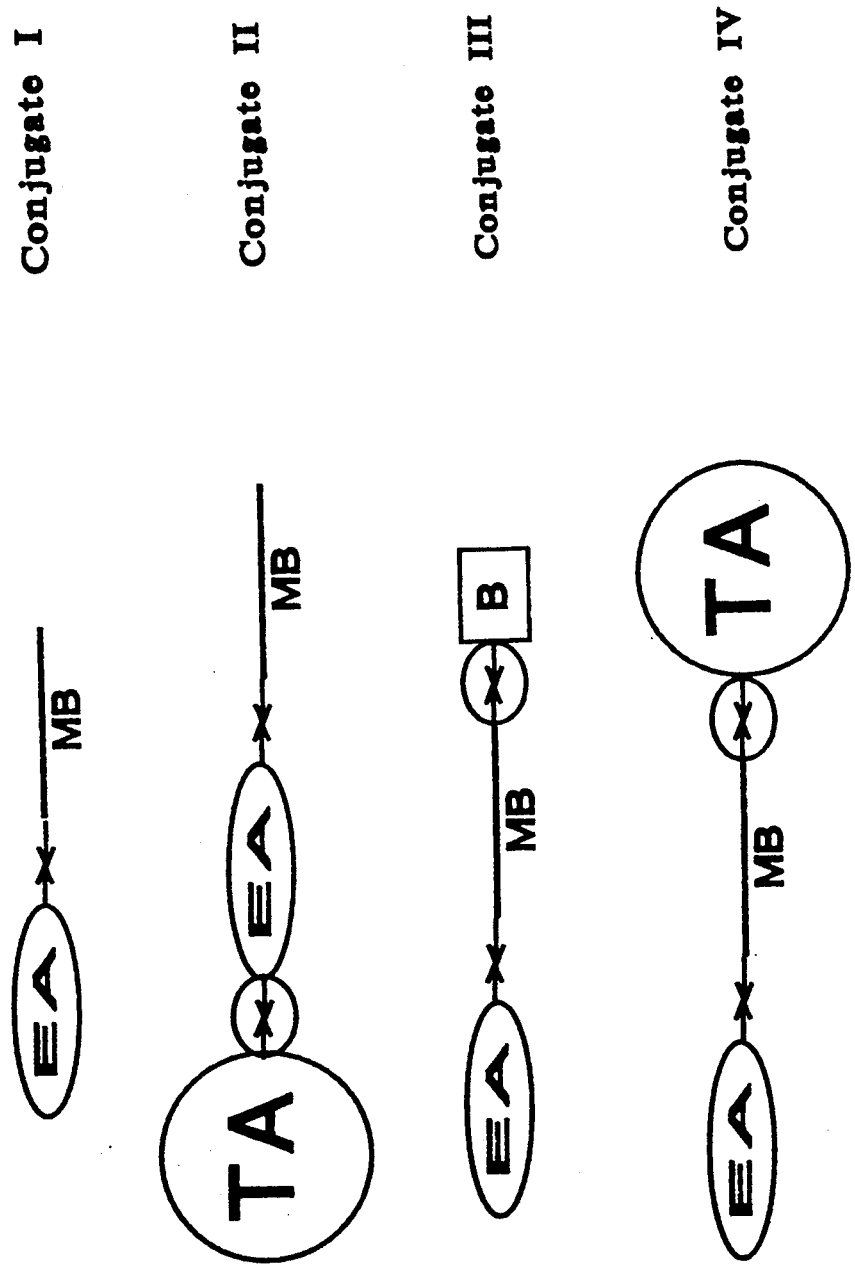

Molecular conjugates of this invention can be further illustrated by the schematic presentations in the figures. FIG. 1 shows the symbols used to depict the molecular conjugates. FIG. 2 shows four different molecular conjugates. Conjugates I and II contain membrane blending peptides in an active form (unblocked), while conjugates III and IV contain membrane blender peptides in an inactive precursor form in accordance with the principles of the invention. In the latter two conjugates, the membrane blending peptide is irreversibly linked to the drug (effector therapeutical agent) and cleavably linked to the blocking agent.

4. Membrane blending agents themselves as effector or labeling agents

Membrane blending agents themselves can be employed therapeutically (or diagnostically). One potential therapeutical use is to eliminate diseased cells. For example, a membrane blending agent targeted for a certain cell may cause the fusion among adjacent target cells to form multinucleated syncytia leading to their death. Another possibility is that they form ion channels causing lethal ion permeability.

When membrane blending agents are used as therapeutical agents in conjunction with targeting agents, it is not crucial that all cells in the target tissue express the targeting antigen or receptor. The membrane blending agents are carried to the target tissue and released. They react with cells in situ independently of the targeting antigen or receptor.

Along this idea, a universal labeling or tagging agent, such as a highly antigenic, unique peptide, can be brought to react with all cells in the target tissue. After this step is achieved in a therapeutical or in vivo diagnostic procedure, an immunotoxin (for therapy) or a radioactive isotope (for radioimaging) or a paramagnetic element (for NMR imaging)-conjugated antibody, which is specific for the labeling agent, is then administered. The advantage for this procedure is that the therapeutical agent or the diagnostic agent for all diseased cells are the same.

Figure 3:
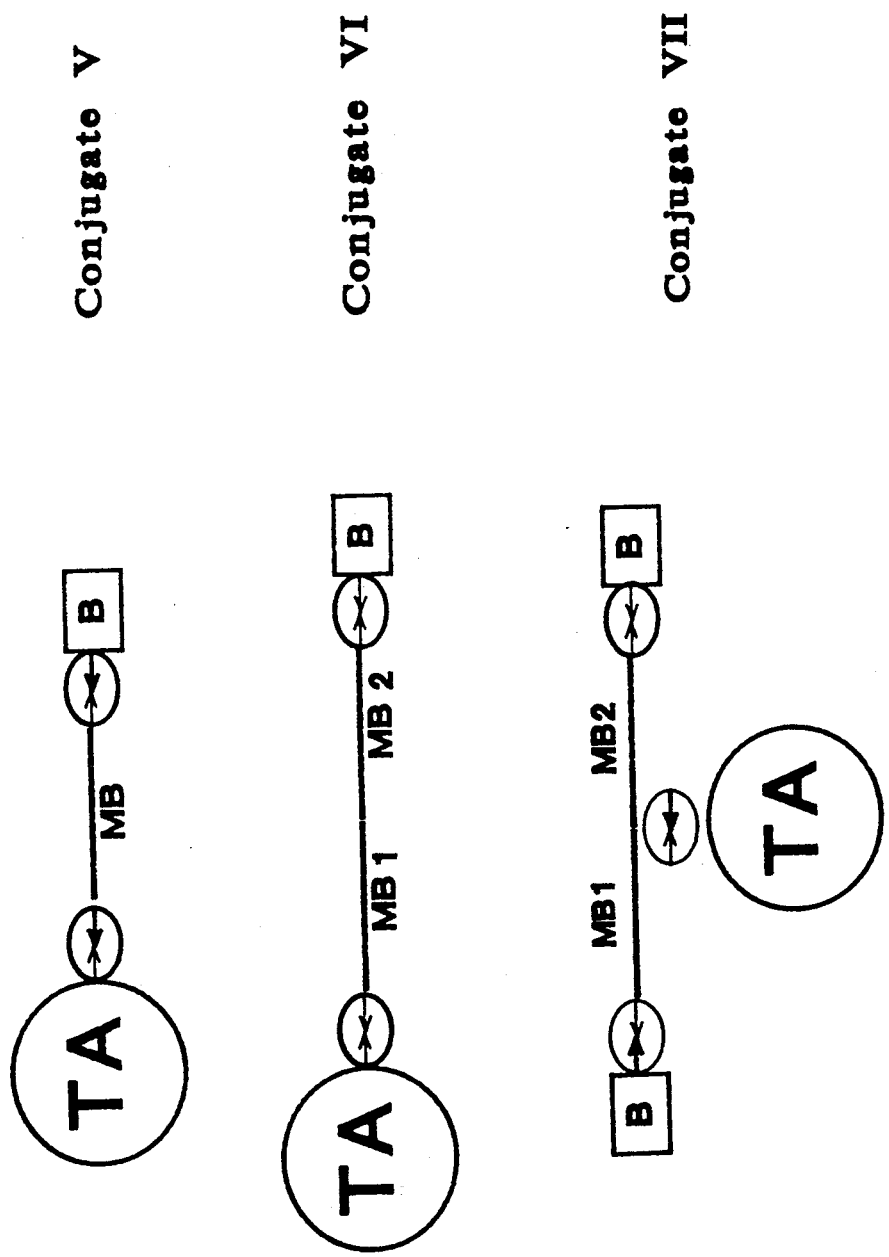

For therapy with membrane blending agents, the several representative molecular conjugates shown in FIG. 3 can be employed. In each conjugate, the membrane blending agent is in inactive "precursor" form. As shown in conjugates VI and VII, two membrane blending agents may be interlinked either cleavably or uncleavably. The agents may be the same or different types. For example, two fusogenic peptides or a fusogenic and an ion channel-forming peptide may be linked together. To increase the aqueous solubility of the conjugates, a stretch of polar amino acid residues can be incorporated between the two membrane blending peptides. Conjugates such as VI or VII may attain the property of reacting with two adjacent cells. In this regard, conjugates prepared from multi-branched molecules such as dextran are also of interest.

5. Membrane blending agents with bifunctional or multifunctional linking groups

Figure 4:
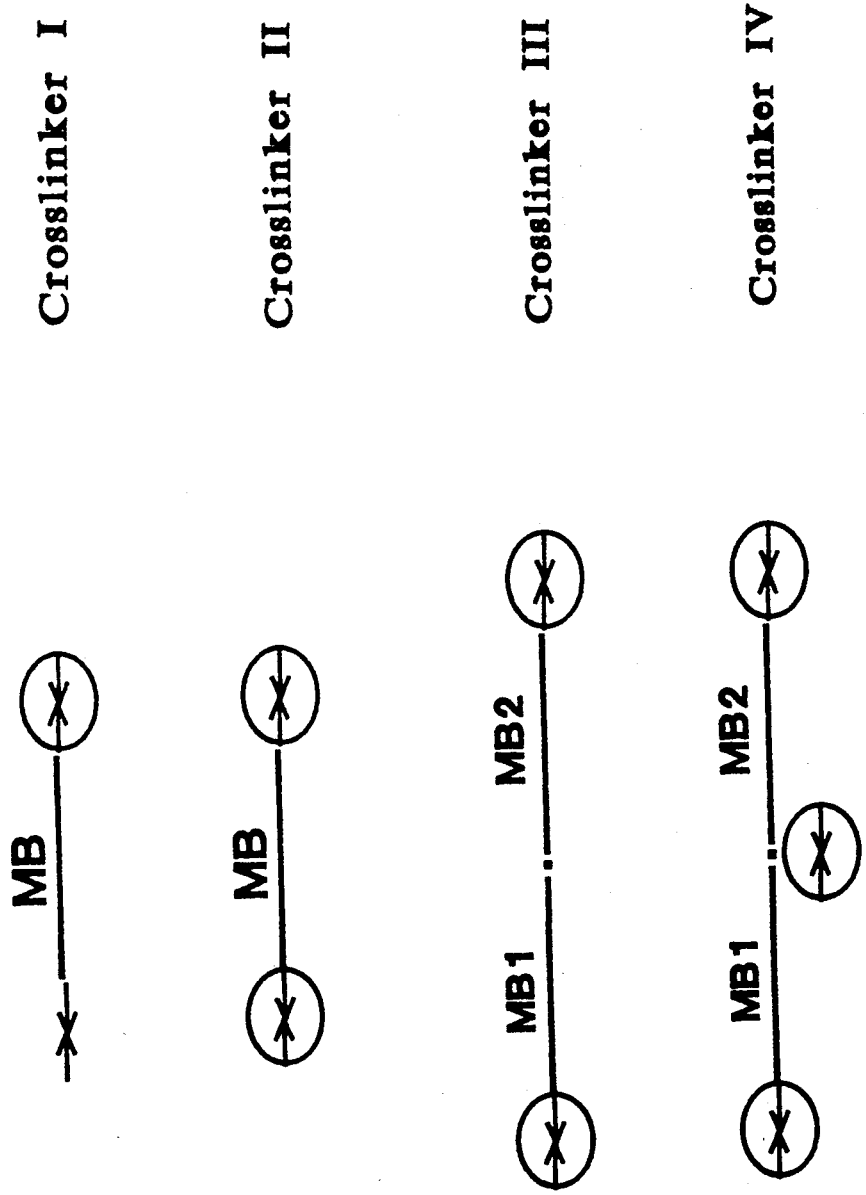

According to the concepts described in the preceeding sections, the preparation of conjugates, in which the membrane blending agents are in inactive precursor form, (e.g. conjugates III–VII). Generally this involves linking the membrane blending agent on both ends. For construction of the molecular conjugates of this invention, membrane blending agents can be prepared with appropriate functional linkers at two ends. These constructs are shown in FIG. 4. In crosslinker type IV, three linking groups are introduced. As discussed in the preceeding section, the two membrane blending peptides in crosslinker III and IV may be of the same or different types. In addition, the linker groups can be either of the irreversible or cleavable types, and may be the same or different linkers, depending on the requirement in conjugate preparation and on the intended pharmacological effects of the conjugates.

The invention is further illustrated by the following examples.

EXAMPLES

Example 1

Preparation of a Crosslinker Composing A Membrane Blending Peptide And Two Functional Linkers A membrane blending crosslinker employing the peptidic segment in the envelope protein gp120 of HTLV-IIIB strain of human immunodeficiency virus (HIV) that is proposed to be involved in the fusion of HIV with target cells. This crosslinker is of type I shown in FIG. 4. The sequence comprises 20 amino acid residues (#508–527) from gp120 and an additional lysine residue at the C terminal. Also, lysine 513 is replaced by arginine. The inclusion of lysine residue is to allow the introduction of linking group.

The crosslinker is synthesized as follows:

Step 1

The synthesis of Fmoc-protected peptide

Fmoc-RERRAVGIGALFLGFLGAAGK-CONH$_2$     (I)

Step 2

Reaction of the Fmoc-protected blender peptide with N-succinimidyl 3-(2-pyridyldithio) propionate (SPDP).

Fmoc—RERRAVGIGALFLGFLGAAGK—CONH$_2$ + SPDP $\xrightarrow{pH\ 9-10}$

Fmoc—RERRAVGIGALFLGFLGAAG$\overset{|}{K}$—CONH$_2$
NHCO—(CH$_2$)$_2$—S—S—(2-pyridyl)
(II)

Step 3

Reaction of I with 50% Diethylamine/DMSO to deprotect the N-terminal R.

II 50% diethylamine/DMSO ⟶ NH$_2$—RERRAVGIGALFLGFLGAAG$\overset{|}{K}$—CONH$_2$
NHCO—(CH$_2$)$_2$—S—S—(2-pyridyl)
(III)

Step 4

Reaction of III with excess homobifunctional succinimidyl, or with heterobifunctional crosslinker with succinimidyl and photoactivatable functional groups. Either crosslinker containers a disulfide bond.

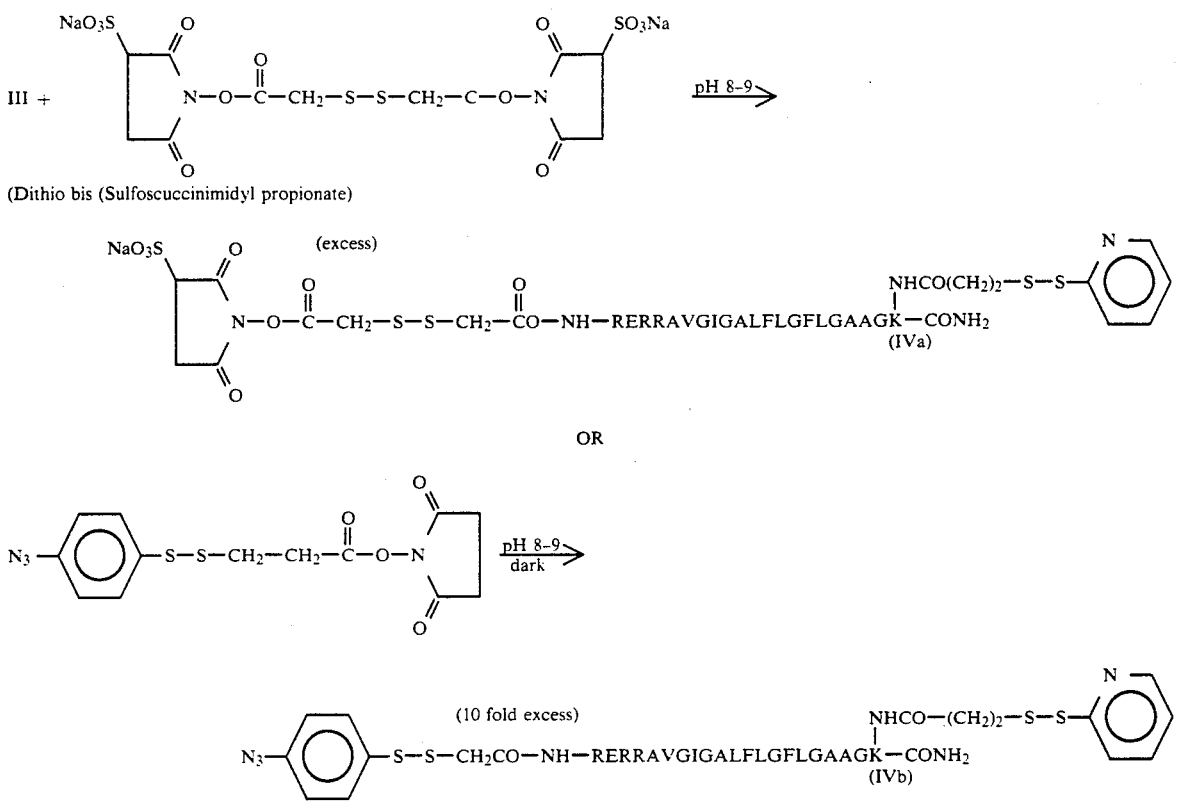

(Dithio bis (Sulfoscuccinimidyl propionate)

(excess)
(IVa)

OR (10 fold excess)
(IVb)

Example 2

Preparation Of A Molecular Conjugate Composing A Therapeutical Agent, A Targeting Agent, And A Membrane Blender In this example, we employ the cross-linker prepared in Example 1 (Cross-linker TVa) to construct a complex with pokeweed antiviral peptide (PAP) and a monoclonal antibody, BAT123, specific for gp120 of HTLV-IIIB. The application of this molecular conjugate is to kill HIV-1-infected cells. Cross-linker TVa is abbreviated as:

(IVa)

Step 1: Reaction of Cross-linker TVa with BAT123 monoclonal antibody with TVa.

(V)

Step 2: Reaction of Conjugate V with PAP.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A molecular conjugate, comprising a macromolecular drug linked to a substantially hydrophobic membrane blending agent which can blend with an insert into a cellular membrane, the agent being cleavably linked to a blocking agent which blocks the ability of the membrane blending agent to insert into a cellular membrane.

2. A molecular conjugate of claim 1, wherein the drug is a polypeptide, protein, glycoprotein or nucleic acid.

3. A molecular conjugate of claim 1, wherein the membrane blending agent which can insert into a cellular membrane is a fusogenic peptide or a portion thereof.

4. A molecular conjugate of claim 3, wherein the fusogenic peptide has the amino acid sequence:

RERRAVGIGALFLGFLGAAGK.

5. A molecular conjugate of claim 1, wherein the blocking agent is also a targeting agent.

6. A molecular conjugate of claim 5, wherein the targeting agent is an antibody specific for a cellular surface antigen.

7. A molecular conjugate of claim 1, wherein the cleavable linkage between the membrane blending agent and the blocking agent is a disulfide linkage.

8. A molecular conjugate comprising a fusogenic peptide having the amino acid sequence RERRAV-GIGALFLGFLGAAGK cleavably linked to a blocking agent which blocks the ability of the fusogenic peptide to insert into a cellular membrane.

9. A molecular conjugate comprising two interlinked substantially hydrophobic membrane blending agents which can blend with and insert into a cellular membrane, in which the membrane blending agents are cleavably linked to blocking agents that block the ability of the interlinked membrane blending agent to insert into the cellular membrane.

10. The molecular conjugate of claim 1 wherein the membrane blending agent is a fatty acid.

11. The molecular conjugate of claim 10 wherein the fatty acid is palmitic acid.

* * * * *